United States Patent [19]

Di Schiena et al.

[11] Patent Number: 4,859,658

[45] Date of Patent: Aug. 22, 1989

[54] COMPOUND COMPOSITIONS WITH IMPROVED ANALGESIC ANTIPYRETIC AND ANTI-INFLAMMATORY ACTIVITY

[75] Inventors: Michele G. Di Schiena, Cisliano, Italy; Zvi Paster, Givataim, Israel

[73] Assignees: Ricerfarma S.R.L., Milan, Italy; Life Science Research Israel Ltd, Ness Ziona, Israel

[21] Appl. No.: 162,127

[22] Filed: Feb. 29, 1988

[30] Foreign Application Priority Data

Mar. 2, 1987 [GB] United Kingdom ................ 8704839

[51] Int. Cl.$^4$ ..................... A61K 31/40; A61K 31/60; A61K 31/02

[52] U.S. Cl. .................................. 514/159; 514/161; 514/420

[58] Field of Search ....................... 514/159, 161, 420

[56] References Cited

U.S. PATENT DOCUMENTS

| | | | |
|---|---|---|---|
| 4,044,125 | 8/1977 | Walkling | 514/161 |
| 4,200,631 | 4/1980 | Ezer et al. | 514/161 |
| 4,228,161 | 10/1980 | Shen | 514/420 |

Primary Examiner—Stanley J. Friedman
Attorney, Agent, or Firm—Oblon, Spivak, McClelland, Maier & Neustadt

[57] ABSTRACT

Pharmaceutical compositions containing thioacetamol and an amount of a non-steroidal anti-inflammatory drug selected from aspirin, indomethacin, dichlofenac, naproxen, sulindac and fenbufen potentiate the activity of these drugs and reduce their undesiderable side-effects.

13 Claims, No Drawings

COMPOUND COMPOSITIONS WITH IMPROVED ANALGESIC ANTIPYRETIC AND ANTI-INFLAMMATORY ACTIVITY

This invention is directed to improved compositions useful as analgesic, anti-pyretic or anti-inflammatory agents either in human or veterinary therapy.

Thiocetamol, p-acetamidophenyl thiophene-2-carboxylate, is a known compound described in GB-A-No. 1585047 (Anphar S. A.). It is therapeutically useful as an analgesic and anti-pyretic agent in treatment of the common cold or influenza. Moreover, its acute median lethal dose ($LD_{50}$) is far lower than that of the parent paracetamol because of its remarkable lower toxicity towards the hepatic parenchyma.

Aspirin, indomethacin, diclofenac, naproxen, sulindac and fenbufen (henceforward designated FANS) are, on the other hand, all well known compounds, therapeutically useful as analgesic, antipyretic and anti-inflammatory non-steroidal drugs. Unfortunately, however, these drugs may all cause a variety of undesirable side effects including in some cases, especially when aspirin or indomethacin is administered, a painless bleeding from the gastrointestinal tract.

There is a serious need, therefore, for more potent and less harmful systemic drugs which can produce a considerable therapeutic effect by the administration of small doses of the drug. It has now been surprisingly found that thiocetamol enhances the effectiveness of drugs such as indomethacin or aspirin by potentiating the properties of these drugs and reducing the known undesirable side effects such as reducing their ulcerogenic effects. By potentiation of the anti-inflammatory, analgesic or anti-pyretic activity, it is possible to use smaller amounts of each drug in combination and thereby reduce the drugs given compared to each drug alone.

Accordingly, the present invention provides a pharmaceutical or veterinary composition which comprises, active ingredients, p-acetamido-phenyl thiophene-2-carboxylate and a non-steroidal anti-inflammatory drug selected from aspirin, indomethacin, diclofenac, naproxen, sulindac and fenbufen.

It is thus possible to provide a pharmaceutical composition containing thiocetamol and an amount of a non-steroidal anti-inflammatory drug selected from aspirin, indomethacin, diclofenac, naproxen, sulindac and fenbufen which is smaller than that which would be necessary to exhibit approximately the same analgesic, anti-pyretic and/or anti-inflammatory activity in the absence of the thiocetamol.

When the non-steroidal anti-inflammatory drug (FANS) is aspirin, typically the composition contains thiocetamol and aspirin in a weight ratio of from 1:0.2 to 1:3, preferably from 1:05 to 1:2 and most preferably about 3:2. Generally the composition contains from 50 to 100 mg/kg of thiocetamol, preferably about 75 mg/kg.

Alternatively, the FANS may be indomethacin. In such an instance, the composition typically contains thiocetamol and aspirin in a weight ratio of from 1:0.002 to 1:0.02, preferably from 1:0.004 to 1:0.01 and most preferably about 150:1. Generally, the composition contains from 100 to 200 mg/kg of thiocetamol, preferably about 150 mg/kg.

The thiocetamol and FANS need not necessarily be given concomitantly in the same composition. They may be administered to a patient separately over a period of time or simultaneously in separate compositions. To this end, the invention also provides products containing p-acetamido-phenyl thiophene-2-carboxylate and a non-steroidal anti-inflammatory drug selected from aspirin, indomethacin, diclofenac, naproxen, sulindac and fenbufen as a combined preparation for simultaneous or sequential use as an analgesic, antipyretic and-/or anti-inflammatory agent.

Thiocetamol and FANS can therefore be administered to a patient in association as an analgesic, antipyretic and/or anti-inflammatory agent. Less of each may be used than would be the case if one was administered on its own without the other. The side-effects normally associated with use of the FANS are therefore reduced or disappear entirely.

Ulcerogenic effect

Gastric complaints, as a result of mucosal irritancy, are among the most common side effects of FANS. The fact is that so far no potent FANS has been reported to be devoid of these intestinal side effects. The results reported here are after single oral doses of various compounds [Menasse R., (1979) Evaluation of ulcerogenic effects—Pharmac. Ther. Vol. 5, pp 191–197, Pergamon Press].

| Compound | Dose mg/kg | Gastric lesions % | Intestinal lesions % |
|---|---|---|---|
| Aspirin | 100 | 0 | 0 |
|  | 300 | 60 | 10 |
|  | 600 | 100 | 10 |
| Indomethacin | 3 | 0 | 0 |
|  | 10 | 100 | 30 |

The $ED_{50}$ of each compound alone, as reported by Maruyama Y. et al [(1981)—Arzneim. Forsch.) Drug Res., Vol. 31 (II) No. 7, pp 1111–1118], are:

TABLE 1

| Compound | $ED_{50}$ mg/kg |
|---|---|
| Aspirin | 500 |
| Indomethacin | 3.6 |
| Ibuprofen | 60 |
| Diclofenac | 5 |

TABLE 1:
Anti-inflammatory effect of Combination of Thiocetamol with Indomethacin
(rat paw oedema test)

I. TEST MATERIALS: Thiocetamol, Indomethacin (Indomet)
II. METHOD:
  1. The test drugs, suspended in 1% methyl cellulose (MC), were administered by oral gavage to groups of male rats (6 rats/group). Controls were given MC only.
  2. Three hours following the test drug administration, 0.1 ml carrageenin (1% in saline) was injected sub-plantar into the right hind paw. Identically saline-injected left hind paw served as control.
  3. Readings were taken on each paw 3 hours following injection of the test drug. The volume of both hind paws was measured with an Hg-displacement Volumeter (Huge, Basile, Italy).
III. DATA EVALUATION Evaluation of anti-inflammatory activity was based on the difference in volume ($\Delta V$) between the right (carrageenin-induced oedema) and left (saline-control) hind paws.
Data was calculated by ranking $\Delta V$ values obtained in drug-treated and control rats and expressed percent increase over control for normal

TABLE 1-continued and inflammed paw, according to:

$$\frac{\text{Rank-sum (Exptl.)}}{\text{Rank-sum (Control.)}} \times 100$$

IV. RESULTS*

A.

| | THIOCETAMOL (mg/kg) | | |
|---|---|---|---|
| | 150 | 300 | 600 |
| ΔV | 90% | 70% | 62% |

B.

| | INDOMET (mg/kg) | | |
|---|---|---|---|
| | 1 | 2 | 4 |
| ΔV | 85% | 63% | 58% |

C.

| | THIOCETAMOL & INDOMET (mg/kg) |
|---|---|
| | 150 + 1 |
| ΔV | 52% |

The test carried out is a well known established one used to evaluate anti-inflammatory activity.

The combination of Thiocetamol with Indomethacin reduces the dose of Indomethacin required alone.

The anti-inflammatory dose of Indomethacin ($ED_{50}$) is, as reported, 3.5 mg/kg.

The combination with Thiocetamal with Indomethacin requires low doses of Indomethacin to induce anti-inflammatory effect and, practically, the dose of that drug in combination with Thiocetamol, is far below its ulcerogenic dose.

It must be also pointed out that the combination of very low doses of each component is not toxic. As a matter of fact Thiocetamol was tested for 4 weeks at a dose of 500 mg/kg without any toxic effects. Moreover, $LD_{50}$ of Thiocetamol is around 2000 mg/kg and that of Indomethacein is 15.2 mg/kg.

No adverse effects were observed in our pharmacological experiments which all proved the efficacy of the administered combination.

TABLE 2

Anti-pyretic effect of Combination of Thiocetamol with Aspirin (yeast-induced) test in rats I. TEST MATERIALS: Thioacetamol, Aspirin II. METHOD:
1. Fever in test animals was induced by subcutaneous injection of yeast (10% in saline). Basal rectal temperature (BRT) was determined in all test animals with the aid of a YSI thermistor probe
2. Four hours after the yeast injection a test drug suspended in 1% methyl cellulose (MC), was administered by oral gavage to groups of male rats (8 rats/group). Controls were given MC only.
3. Measurements of rectal temperatures (ERT) in response to the various treatments, were carried out at 1, 3 and 5 hours after the test drug administration.

III. DATA EVALUATION

Evaluation of anti-pyretic activity was based on the temperature difference (Δt) between BRT and ERT at each of the three respective test periods for each treatment group.
Data was calculated by ranking Δt values obtained in test drug-treated and control rats and expressed in percent as the following ratio:

$$\frac{\text{Rank-sum (Exptl.)}}{\text{Rank-sum (Control)}} \times 100$$

IV. RESULTS*

A.

| | | THIOCETAMOL (mg/kg) | | |
|---|---|---|---|---|
| | | 75 | 150 | 300 |
| Δt at: | 1 hour | 86% | 47% | 26% |
| | 3 hour | 91% | 96% | 40% |
| | 5 hour | 91% | 84% | 61% |

B.

| | | ASPIRIN (mg/kg) | | |
|---|---|---|---|---|
| | | 50 | 100 | 200 |
| Δt at: | 1 hour | 86% | 67% | 49% |
| | 3 hour | 83% | 55% | 29% |
| | 5 hour | 67% | 56% | 19% |

C.

| | | THIOCETAMOL & ASPIRIN (mg/kg) |
|---|---|---|
| | | 75 + 50 |
| Δt at: | hour | 51% |
| | 3 hour | 41% |
| | 5 hour | 51% |

As shown by the test on Table 2 a good anti-pyretic effect can be obtained, using the compounds combined, with an Aspirin dose far below the $ED_{50}$ of Aspirin when administered alone and without any ulcerogenic or toxic side effects ($LD_{50}$ of Aspirin is 1000 mg/kg).

The compositions of the present invention consist of a combination of Thiocetamol with one of the above mentioned FANS, preferably in an intimate admixture with a pharmaceutically acceptable carrier or diluent according to conventional pharmaceutical techniques. The carrier may take a wide variety of forms depending upon the form of preparation desired for administration i.e. oral or parenteral.

In preparing the compositions in oral dosage from any of the usual pharmaceutical media may be employed such as water, glycols, oils, alcohols, flavouring agents, preservative coloring agents and the like in the case of oral liquid preparations such as suspensions, elixirs and solutions. Carriers such as starches, sugars, diluents, granulating agents, lubricants, binders, disintegrating agents and the like can be employed in the case of solid oral preparations such as, for example, powders, capsules or tablets. Because of their ease in administration, tablets and capsules represent the most advantageous oral dosage unit form. If desired, the tablets may be sugar coated or enteric coated by standard techniques.

For parenterals, the carrier will usually comprise sterile water, although other ingredients may be added to aid solubility or for preservative purposes.

Injectable suspensions may also be prepared, in which case appropriate liquid carriers, suspending agents and the like may be employed.

An association with different and complementary drugs, such as antibiotics, anti-hystaminics, mucolytics, caffeine and theobromine can be also advantageous.

EXAMPLE 1

Small paper bags each containing as active ingredients: Aspirin 0.050 g—thiocetamol 0.075 g

Formula

| Aspirin | 10.0 g |
|---|---|
| Thiocetamol | 15.0 g |
| Carboxymethylcellulose | 50.0 g |
| Lactose | 100.0 g |
| Erythrosine | 0.2 g |
| Orange powdered essence | 4.0 g |
| Lemon powdered essence | 4.0 g |
| Saccharose | 1000 g |

Procedure

Thioacetamol, aspirin, carboxymethyl cellulose and saccharose were milled for 30 minutes together to obtain a very fine powder which was passed through a screen with an opening of 1.0 mm. The resulting granulate was mixed with a 50% hydroalcoholic solution of the essences and erythrosine the obtained wet paste was milled again for an hour and then passed through a screen with an opening of 1.0 mm.

The resulting granulate was dried at a temperature of 30° C. in dry air and then filled in small paper bags of appropriate size using a corresponding filling machine.

EXAMPLE 2

Gelatin capsules, each containing Indomethacin 0.04 g—Thiocetamol 0.600 g.

Formula

| Indomethacin | 4.0 g |
|---|---|
| Thiocetamol | 600.0 g |
| Sodium lauryl sulphate | 1.0 g |
| Rice starch | 300.0 g |
| Magnesium stearate | 60.0 g |
| Titanium dioxide | 10 g |
| Microcristalline cellulose | 25.0 g |

Procedure

All solid materials were milled together to obtain a fine powder which was compacted in a compacting machine and then passing through a screen with an opening of 0.6 mm. and filled in gelatin capsules of appropriate size, each containing 1.0 g of mixture using a corresponding filling machine.

EXAMPLE 3

Anti-pyretic tablets, each containing Aspirin 0.05 g and Thiocetamol 0.075 g.

Formula

| Aspirin | 100.0 g |
|---|---|
| Thioacetamol | 150.0 g |
| Magnesium stearate | 300.0 g |
| Colloidal silicon dioxide | 300.0 g |
| Microcrystalline cellulose | 50.0 g |
| Lactose | 100.0 g |

Procedure

The solid materials were milled together for 30 minutes to obtain a fine powder.

This was compacted in a compacting machine and passed through a screen with an opening of 1.0 mm.

The resulting granulate was compressed using a capsule formed die and concave punches.

We claim:

1. A pharmaceutical or veterinary composition which comprises, as active ingredients, p-acetamido-phenyl thiophene-2-carboxylate and a non-steroidal anti-inflammatory drug selected from the group consisting of aspirin and indomethacin, wherein said composition contains p-acetamido-phenyl thiophene-2-carboxylate and aspirin in a weight ratio of from 1:0.2 to 1:3 or p-acetamido-phenyl thiophene-2-carboxylate and indomethacin in a weight ratio of from 1:0.002 to 1:0.02.

2. A composition according to claim 1, which contains p-acetamido-phenyl thiophene-2-carboxylate and aspirin in a weight ratio of from 1:0.2 to 1:3.

3. A composition according to claim 2, wherein the weight ratio is from 1:0.5 to 1:2.

4. A composition according to claim 3, wherein the weight ratio is about 3:2.

5. A composition according to any one of claims 2 to 4, which contains from 50 to 100 mg/kg of p-acetamido-phenyl thiophene-2-carboxylate.

6. A composition according to claim 5, which contains about 75 mg/kg of p-acetamido-phenyl thiophene-2-carboxylate.

7. A composition according to claim 1, which contains p-acetamido-phenyl thiophene-2-carboxylate and indomethacin in a weight ratio of from 1:0.002 to 1:0.02.

8. A composition according to claim 7, wherein the weight ratio is from 1:0.004 to 1:0.01.

9. A composition according to claim 8, wherein the weight ratio is about 150:1.

10. A composition according to any one of claims 7 to 9, which contains from 100 to 200 mg/kg of p-acetamido-phenyl thiophene-2-carboxylate.

11. A composition according to claim 10, which contains about 150 mg/kg of p-acetamido-phenyl thiophene-2-carboxylate.

12. A composition according to any one of the preceding claims, which includes one or more other substances selected from antibiotics, anti-hystaminics, mucolytics, caffeine and theobromine.

13. A composition according to any one of the preceding claims, which further comprises a pharmaceutically or veterinarily acceptable carrier or diluent.

* * * * *